United States Patent [19]

Kammann, Jr. et al.

[11] 4,380,499

[45] Apr. 19, 1983

[54] SULFURIZED FATTY OIL ADDITIVES AND THEIR USE IN A LUBRICATING OIL AND A FUEL

[75] Inventors: Karl P. Kammann, Jr., Crown Point, Ind.; Marvin J. Den Herder, Olympia Fields, Ill.

[73] Assignee: Ferro Corporation, Cleveland, Ohio

[21] Appl. No.: 291,545

[22] Filed: Aug. 10, 1981

[51] Int. Cl.$^3$ .................... C10M 1/20; C10M 1/38; C10L 1/18; C10L 1/24
[52] U.S. Cl. .................... 252/48.6; 44/66; 260/399
[58] Field of Search .................... 252/48.6; 44/66; 260/399

[56] References Cited

U.S. PATENT DOCUMENTS

| | | | |
|---|---|---|---|
| 2,311,929 | 2/1943 | Chenicek et al. | 44/66 |
| 3,455,896 | 7/1969 | Den Herder et al. | 252/48.6 |
| 3,740,333 | 6/1973 | Hutchinson et al. | 252/48.6 |
| 3,850,825 | 11/1974 | Vienna et al. | 252/48.6 |
| 4,134,845 | 1/1979 | Wakim | 252/48.6 |

*Primary Examiner*—W. J. Shine
*Attorney, Agent, or Firm*—Philip Hill

[57] ABSTRACT

Improved lubricant additive compositions, derived from fatty oils, comprise sulfurized, transesterified triglycerides. Such additive compositions possess improved solubility in oils and impart improved lubrication properties to both lubricant and fuel compositions.

35 Claims, No Drawings

SULFURIZED FATTY OIL ADDITIVES AND THEIR USE IN A LUBRICATING OIL AND A FUEL

BACKGROUND OF THE INVENTION

It has been common practice to include in lubricant formulations additives to provide improved antiwear and rust inhibition properties. In the past, sulfurized triglycerides, such as sulfurized lard oil, have been utilized, especially in association with lightly refined aromatic mineral oils which provided sufficient solubility for the sulfurized triglycerides.

With the increased concern for toxicity of aromatic compounds found in such mineral oils, lubricant formulations now comprise essentially non-aromatic oils. This change to substantially non-aromatic base oils created a major problem, resulting from a significant decrease in solubility of the sulfurized triglycerides in the non-aromatic mineral oil, resulting in solidification and/or dropout of the sulfurized triglycerides.

While the solubility problem has been overcome, the modified lubricant products have been found to be either deficient in desirable lubricant properties or incapable of providing needed improvement in these properties.

In a typical approach to this problem, as reported in U.S. Pat. No. 3,455,896, sulfurized, low molecular weight polybutenes were reacted with liquid triglycerides, which were susceptible of sulfurization, to yield an additive. In U.S. Pat. No. 3,850,825, another additive was prepared by the sulfurization of a mixture of prime burning lard oil and alkyl oleate. In U.S. Pat. No. 3,740,333, $C_{10}$–$C_{16}$ alcohol esters of unsaturated fatty acids, having 18 to 22 carbon atoms, were blended with a triglyceride and either used "as is" or sulfurized. Modifications of such compositions have been reported in U.S. Pat. Nos. 4,149,982, 4,166,795, 4,166,796, 4,166,797, and 4,188,300.

Although these prior art efforts have increased the solubility of sulfurized fatty oils to acceptable values, there has remained a serious need for sulfurized additives possessing both good solubility and a combination of improved lubricant properties, such as, for example, better low temperature flow properties, better load carrying and antifriction properties, and a lack of sludging. Such improved lubricant properties would also be attractive for use in various fuels systems employed for power generation and heating purposes.

SUMMARY OF THE INVENTION

This invention relates to improved lubricant additive compositions comprising sulfurized fatty oils, to the process for their preparation, and to oil product compositions, including both fuels and lubricants, incorporating such sulfurized fatty oils. The additive compositions of this invention exhibit highly desirable solubility properties when employed in either lubricant or fuel formulations. The particularly desirable utility of these additive compositions derives from their providing generally improved performance characteristics, ranging from improved load carrying, antiwear, and friction properties, to reduced levels of deposits and varnish, and to improved pour-point depression.

This invention particularly relates to sulfurized, fatty oil additive compositions, comprising a sulfurized, transesterified triglyceride wherein the total acid component of the triglyceride comprises no less than about 35 mole % saturated aliphatic acids and no more than about 65 mole % unsaturated fatty acids, said total acid component being further characterized as comprising:

(a) more than about 20 mole % of mono-unsaturated acids;
(b) less than about 15 mole % of poly-unsaturated fatty acids;
(c) more than about 20 mole % saturated aliphatic acids having 6 to 16 carbon atoms, including more than about 10 mole % saturated aliphatic acids having 6 to 14 carbon atoms; and
(d) less than about 15 mole % saturated aliphatic acids having 18 or more carbon atoms.

This invention further relates to the method for preparation of such transesterified and sulfurized triglycerides.

This invention additionally relates to lubricant and fuel compositions incorporating such sulfurized, fatty oil additives, whereby improved performance in conventional usages is achieved. The additives of this invention may be employed in concentrations up to about 15 wt. % in lubricant formulations and up to about 0.1 wt. % in fuel compositions.

DESCRIPTION OF THE INVENTION

This invention is directed to additive compositions of sulfurized fatty oils, and to the process of preparing said compositions, which exhibit the required solubility properties in non-aromatic base oils without the disadvantages associated with the prior art lubricant additive formulations. In addition, the compositions of this invention exhibit improved performance characteristics, over the compositions of the prior art, including improved load carrying, antiwear, and friction properties, reduced levels of deposits and varnish in used oils, and better pour-point depression. This invention is likewise directed to lubricant and fuel formulations which include the inventive additive compositions.

Triglycerides of the prior art, typically derived from plants and animals, do not provide maximum effectiveness as lubricant additives because of the chain length and/or the degree of unsaturation of the acid moiety. Modification of said acid moieties of the triglycerides, by transesterification, produces novel triglycerides that optimize the properties of the resulting additive when said novel triglycerides are coupled, through sulfur bonds, with solubilizing components, such as esters and/or olefins.

The acid moiety of the triglyceride components of the additives of this invention consists of an acid mixture having less than about 65 mole % unsaturated acids, mainly possessing one ethylenic carbon-carbon double bond, and more than 35 mole % saturated aliphatic acids. Of the total acid moiety, less than about 15 mole % are saturated acids having 18 or more carbon atoms and more than about 35 mole % are saturated acids having less than 18 carbon atoms. Similarly, less than about 15 mole % are poly-unsaturated acids and more than about 20 mole % are mono-unsaturated acids.

The transesterification reaction is carried out on blends of (1) triglycerides, (2) triglycerides and organic acids, or (3) triglycerides and esters of organic acids. Where acids are included in the reaction and the amount of free acids present in the transesterified blend is greater than about 15%, then the free acid is preferably esterified with monoalcohols, glycols or glycerol to decrease the free acid content prior to the subsequent sulfurization reaction. The esterification of free acids may also be effected when the concentration thereof is less than about 15% but this is not imperative.

Following the transesterification, or esterification, the reaction components are coupled by reaction with sulfur with, where desired, the added presence of solubilizing components, such as esters, olefins or blends thereof. The sulfurization is conducted in accordance with known procedures which generally consist of heating the mixture with elemental sulfur at temperatures from about 300° F. to about 400° F. for from about 1 to about 8 hours. The sulfur content of the additives of this invention should be within the range from about 4 to about 14 wt. %.

The additives of the present invention preferably utilize as starting compounds naturally occuring triglycerides. The compositions of such triglycerides are detailed in *Bailey's Industrial Oil and Fat Products*, Vol. I, 4th Edition, John Wiley and Sons.

A triglyceride is the ester product of glycerol and one or more fatty acids, represented schematically as

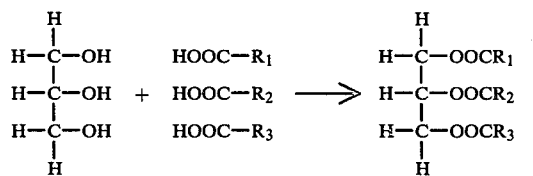

where $R_1$, $R_2$, and $R_3$ represent hydrocarbon groups which may be identical or different in chain length and may also be saturated or unsaturated.

Triglycerides from fish and animal oils contain acids with chain lengths that normally exceed 15 carbon atoms and usually contain large amounts of mono- and poly-unsaturated acids. Triglycerides from some plant species contain appreciable amounts of shorter chain acids, having 10, 12 or 14 carbon atoms. These shorter chain plant-derived acids tend to be mainly saturated acids.

In the process of preparing the triglyceride components of the additive of the present invention, commercially available triglycerides which do not have the required distribution of acids are transesterified with acids, esters or triglycerides having a higher proportion of the required distribution of acids. The resultant mixtures, following the transesterification, have the required average distribution of acids, preferably as triglycerides. Free acids in the transesterification reaction product may then be esterified with mono-alcohols, ranging from methyl to $C_{20}$, or with poly-alcohols, such as a glycol or glycerol. If the free acid content in the transesterification reaction product is greater than about 15%, esterification is a highly preferred procedure, whereas below the 15% level esterification is optional. Transesterification is preferably carried out in the presence of a strong acid catalyst, at temperatures within the range from about 400° F. to about 450° F. for from about 1 to about 8 hours.

Prior to sulfurization, the transesterified mixture may be blended with a solubilizing component when further improved solubility is desired. Whenever there is a sufficient amount of free unsaturated acid in the transesterification reaction product, the esterification of such acids can provide the solubilizing factor. Otherwise additional solubilizing components, such as unsaturated esters or olefins are added prior to sulfurization.

Although the amount of solubilization component present, prior to sulfurization may, if desired, be as high as about 70 wt. %, such solubilization components, when employed, are preferably present in an amount within the range from about 5 wt. % to about 55 wt. %.

Examples of naturally occurring triglycerides, which may be utilized as starting triglycerides for the preparation of the additives of this invention, include, but are not limited to, lard oil, tallow, palm oil and peanut oil.

The acid moiety of the triglyceride, following transesterification, consists of a total mono- and poly-unsaturated fatty acids in an amount of less than about 65 mole %. The acid moiety consists of more than about 20 mole %, preferably more than about 35 mole %, more preferably less than about 10 mole %, of mono-unsaturated fatty acids and less than about 15 mole % poly-unsaturated fatty acids; i.e., acids having more than one ethylenic carbon-carbon bond. Total saturated aliphatic acids comprise more than about 35 mole %, and preferably more than about 50 mole %, of said acid moiety. Of the total acid moiety, saturated acids having 6 to 14 carbon atoms are present in an amount of more than about 10 mole % and preferably more than about 15 mole %; saturated acids having 6 to 16 carbon atoms including the aforementioned acids having 6 to 14 carbon atoms, are present in an amount of more than about 20 mole % and preferably more than about 35 mole %; and saturated acids having 18 or more carbon atoms are present in an amount of less than about 15 mole %.

The acids utilized are normally straight chain acids, although the presence of some branched chain acids, such as 2-ethylhexanoic and 2-methyldecanoic, is not deleterious.

Almost any alcohol can be utilized in the optional esterification step, including glycerol, diols and monohydroxy alcohols, especially terminal primary alcohols. Branched alcohols, such as 2-ethylhexyl, isodecyl, isododecyl and mixtures containing a wide range of alcohols, such as 11 to 22 carbon atoms, can also be utilized.

Olefins, when used as solubilizing agents, normally contain 8 to 20 carbon atoms per molecule. Olefin mixtures may be employed.

In one embodiment of this invention, the transesterification and esterification is caused to occur in a reduced number of steps by mixing together the starting triglyceride, replacement acids, and alcohol, and then subjecting the mixture to heat in the presence of a transesterification catalyst.

Transesterification catalysts are normally utilized to speed the reaction, although the reaction will proceed without a catalyst. The amount and type of catalyst can be widely varied. Known transesterification catalysts are tetrabutyl titanate, zinc acetate, sodium carbonate, sodium hydroxides, potassium hydroxide, sodium methylate, sodium sulfate, stannous oxalate, p-toluenesulfonic acid (PTSA), methanesulfonic acid (MSA), butylchlorotin dihydroxide, sulfuric acid, phosphoric acid and the like. p-Toluenesulfonic acid and methanesulfonic acid are the preferred catalyst. The amount of catalyst utilized is in the range of about 0.01 wt. % to about 1 wt. % with the preferred range being about 0.03 wt. % to 0.5 wt. %.

Comparison runs made with and without a transesterification catalyst showed the following degree of completion:
 (a) catalyst: 0.15% methanesulfonic acid, 4 hours at 400° F.—about 72% completion;

(b) catalyst: 0.1% butylchlorotin dihydroxide, 8 hours at 400° F.—about 44% completion; and
(c) catalyst: NONE—8 hours at 400° F.—about 21% completion.

The above comparison study shows that the transesterification reaction occurs even in the absence of a catalyst and that the rate of reaction is increased by the addition of a catalyst.

During the transesterification reaction the presence of 0.15 to 1.0 wt. % water increases the rate of transesterification. However, during subsequent esterification it is desirable that the water that had been added, or is generated by the esterification reaction, be removed as promptly as possible, in order to drive the reaction to completion and thus increase the yield.

The following examples serve, without limitation, to describe the invention more fully as it relates to lubricant additive compositions. In the examples all parts and percentages are on a weight basis unless otherwise indicated.

In the following examples HOE alcohol refers to an 11 to 22 carbon alkyl alcohol, averaging about 16 carbons, mainly branched primary alcohol, sold commercially as Heavy Oxo Ends. Emery 876 acid is a saturated acid mixture containing about 11% $C_9$, 2% $C_{10}$–$C_{13}$, 16% $C_{14}$, 1% $C_{15}$, 42% $C_{16}$, 1% $C_{17}$ and 12% $C_{18}$ monobasic acids and 15% $C_6$–$C_{14}$ dibasic acids. Diol concentrate is a mixture of predominantly straight chain alcohols, containing about 84% diols, mainly $C_{13}$–$C_{17}$ primary, and about 16% monohydroxy alcohols, mainly $C_{15}$–$C_{16}$ primary.

EXAMPLE 1

A blend of 67 parts prime lard oil, 28 parts crude coconut oil, and 5 parts oleic acid was heated for 4 hours at 400° to 410° F., in the presence of 0.2% p-toluenesulfonic acids. The acid value (A.V.) of the mixture rose from 16 to 20. Acid value is determined by titration (A.O.C.S. method Cd 3a-63) and is defined as the number of milligrams of potassium hydroxide necessary to neutralize the free acids in one gram of sample.

To the transesterification reaction mixture I was added 8 parts of HOE alcohol and the heating continued for an additional 3 hours. The A.V. value was reduced during this process to 10. The resultant product II, except for small amounts of free acid and alcohol, contained about 87% transesterified triglyceride and about 13% ester.

This product was sulfurized, by heating with elemental sulfur at 360°–370° F. for 3 hours, followed by cooling below 330° F. and passing air through the mixture for about 1.5 hours, to remove any $H_2S$ or other noxious light ends. The resultant product III contained 6.3% bound sulfur.

EXAMPLE 2

Sixty (60%) percent of the transesterified triglyceride product I, obtained by the procedure of Example 1, was blended with 40% of an alkyl alcohol (HOE) ester of unsaturated fatty acids (tall oil fatty acids) and the mixture sulfurized to yield product IV, having 7.3% bound sulfur.

EXAMPLE 3

A blend of 100 parts prime lard oil and 25 parts Emery 621 coconut fatty acid was heated for 4 hours at 400°–410° F., in the presence of 0.2% p-toluenesulfonic acid. To this mixture was added 25 parts HOE alcohol and the mixture was heated for an additional 3 hours. The A.V. of this product V was 11.

To 150 parts of reaction product V was added 20 parts of the alkyl alcohol (HOE) ester of unsaturated fatty acids (tall oil fatty acids) and the mixture sulfurized to yield product VI, having 6.7% bound sulfur.

EXAMPLE 4

A blend of 78 parts of a solid triglyceride, having a melting point of about 100° F., and 22 parts Emery 621 coconut fatty acids was heated at 400°–410° F. for 4 hours, in the presence of 0.2% methanesulfonic acid. Twenty (20) parts of HOE alcohol was added and the reaction continued until the A.V. decreased to 10. Twenty-eight (28) parts of HOE alcohol ester of tall oil fatty acids was then added and the mixture sulfurized to yield product VII, having 6.5% bound sulfur. The mixture, prior to sulfurization, contained about 53% transesterified triglyceride and about 47% HOE ester.

EXAMPLE 5

Sixty-eight (68) parts of a solid triglyceride, having a melting point of about 100° F., was mixed with 19 parts Emery 621 coconut fatty acid and 13 parts tall oil fatty acid. The mixture was heated at 400°–410° F. for 4 hours, in the presence of 0.15% methanesulfonic acid. Thirty (30) parts HOE alcohol was then added and the heating continued until an A.V. of 9 was obtained. The product was then sulfurized, using 6.5% sulfur, to yield the sulfurized product VIII.

EXAMPLE 6

A mixture of 80 parts prime burning lard oil and 20 parts Emery 876 acids was heated for 4 hours at 400°–410° F., in the presence of 0.3% p-toluenesulfonic acid. Twenty-two (22) parts HOE alcohol was then added and the heating continued until an A.V. of 10 was obtained. To this mixture was added 30 parts of a diester prepared from 2 moles of tall oil fatty acids and 1 mole diol concentrate. The resultant mixture was sulfurized to give product IX, containing 7.4% bound sulfur.

EXAMPLE 7

A blend of 12% Chevron $C_{15}$–$C_{18}$ α-olefin and 88% of product V was sulfurized to give product X, containing 7.1% sulfur.

EXAMPLE 8

The procedure of Example 4 was repeated on a large scale, utilizing 6% sulfur in the sulfurization step. The product XI contained 5.9% bound sulfur.

EXAMPLE 9

A blend of 78 parts of a solid triglyceride, having a melting point of about 100° F., and 22 parts Emery 621 coconut fatty acids was heated at 400°–410° F. for 4 hours, in the presence of 0.15% methanesulfonic acid. Twenty-three (23) parts of isodecyl alcohol was then added and the heating continued for an additional 4 hours at 340°–380° F. The A.V. was reduced during this process to 8. Sixteen (16) parts of isodecyl ester of tall oil fatty acids was then added and the mixture sulfurized, by heating with sulfur, using the procedure of Example 1, to yield product XII, containing 6.7% bound sulfur. The mixture prior to sulfurization, except for small amounts of free acid and alcohol, contained about 56% transesterified triglyceride and 44% ester.

The following products were prepared for comparison purposes.

EXAMPLE A

A mixture of 88% prime burning lard oil and 12% methyl oleate was sulfurized to produce product A, containing 9.7% bound sulfur.

EXAMPLE B

A mixture of 55% prime burning lard oil and 45% HOE alcohol ester of tall oil fatty acids was sulfurized to yield sulfurized product B, containing 9.0% bound sulfur and having an A.V. of 9.

EXAMPLE C

A mixture of 50% prime burning lard oil and 50% isodecyl alcohol ester of tall oil fatty acids was sulfurized to yield product C, containing 9.1% bound sulfur and having an A.V. of 8.

Products exemplary of the sulfurized fatty oil additive compositions of this invention, prepared as described in Examples 1-9, above, together with comparison products A and B, were tested by conventional procedures at various concentration levels, ranging from 1 to 4 wt. %, in a mineral oil and in three commercially available engine oils, to determine the respective effects on flow properties. Results are presented in Tables I, II, III, and IV.

The mineral oil contained no pour depressant additive and did not flow at temperatures below 0° F. The engine oils contained pour depressants and still flowed at −20° F. Solubility of the products of this invention in these oils was good.

Table I shows clearly that the additives of this invention have excellent properties as pour depressants, keeping the oil fluid at lower temperatures when added to a mineral oil having a pour point of 0° F. However, when large amounts of the additives are added, the ability to cause flow at low temperatures is reduced.

Tables II, III and IV show that sulfurized fatty oils (Products A and B) diminish the low temperature flow properties of pour depressed engine oils. However, additives of the present invention can be used at higher concentrations without any harmful effect upon the flow properties of the same engine oils.

The improved load carrying and friction reduction properties imparted by the use of the additives of the present invention are illustrated by the data in Tables V and VI, showing the improved load carrying and friction reduction (torque) as measured by the Falex step-up test. Tests presented in Table V were conducted with a pour-depressed engine oil. Tests presented in Table VI illustrate the additive performance with nonformulated base oils, including a mineral oil and a synthetic lubricating oil base stock.

Falex procedures for evaluating lubricants are described in Lubrication Engineering, 24, No. 8, 349-358 (1968). The procedure employed in these tests was as follows:

After a 5 minute warmup at 250 lbs., the load is increased in 250 lb. increments and held at each increment for one minute, until failure, which is of the weld type. Torque comparisons were also made to show differences in friction.

Crankcase oil, formulated to be a high quality SE Grade 10W40 crankcase oil, was evaluated using a four-ball machine in testing for friction and wear as described in the ASTM-D-2266 procedure. The crankcase oil alone was compared with crankcase oil containing 2% additive B or 2% additive XI. Tests were conducted at 1800 R.P.M., using a 40 kg. load, for one hour at 350° F. The results obtained were as follows:

| Additives | Wear-Scar Diameter |
| --- | --- |
| Crankcase Oil | 0.86 |
| + 2% Additive B | 0.80 mm |
| + 2% Additive XI | 0.57 mm |

Several products were tested for solubility in synthetic hydrocarbon oils by dissolving in Gulf Synlube 4cs with warming and stirring. The solutions were then kept at 45° F. for 4 days and finally observed after warming to room temperature. The observed results were:

2% A—Heavy Bottom Layer
2% B—Slight dropout
2% C—Slight dropout
2% VI—Very slight dropout
2% VIII—Tr. Haze
2% VII—Hazy
2% XI—Tr. Haze The sulfurized fatty oil additive compositions of this invention are effective when employed in lubricating oils at concentrations ranging from about 0.05 to about 15 wt. %. The preferred concentration range is generally from about 0.5 to about 5 wt. %.

In other embodiments of this invention the sulfurized fatty oil additive compositions are effective in various types of fuels, particularly to improve the lubrication of fuel pumps; to reduce wear on pistons, rings, and cylinders; and to reduce deposit formation. Such fuels broadly include gasolines, for use in spark-ignition internal combustion engines; diesel oils, for use in compression-ignition internal combustion engines; and heating (or furnace) oils, for use in oil-fired burner assemblies. Other advantages include, when employed in fuel oils or diesel fuels, reduction of pour points and attendant reduction in plugging of oil filters. In such novel and improved fuel compositions, the additives of this invention are effective at relatively low concentrations within the range from about 0.0005 to about 0.1 wt. %, and preferably from about 0.0015 to about 0.05 wt. %.

TABLE I

Low Temperature Flow of a Mineral Oil[(1)]
(viscosity 27 cst. at 40° C.)
After 16 Hours at −18° F.

| Additive | 1% | 2% | 3% | 4% |
| --- | --- | --- | --- | --- |
| A | Flows | No Flow | — | — |
| B | — | Flows | No Flow | — |
| C | — | Flows | No Flow | — |
| VI | — | Flows | No Flow | — |
| VIII | — | Flows | No Flow | — |
| XI | — | Flows | Flows | No Flow |
| XII | — | Flows | Flows | No Flow |

[(1)]Without additives, no flow at 0° F.

TABLE II

Commercial 10W40 Oil "Brand A"[(1)]
After 16 Hours at −20° F.

| Additive | 1% | 2% | 3% | 4% |
| --- | --- | --- | --- | --- |
| A | Flows | No Flow | — | — |
| B | — | Flows[(2)] | No Flow | — |
| C | — | Flows[(2)] | No Flow | — |
| III | — | Flows | No Flow | — |
| IV | — | Flows | Flows | Flows |

TABLE II-continued

Commercial 10W40 Oil "Brand A"[1]
After 16 Hours at −20° F.

| Additive | 1% | 2% | 3% | 4% |
|---|---|---|---|---|
| VI | — | Flows | Flows | Flows[2] |
| VII | — | Flows | Flows | Flows[2] |
| VIII | — | Flows | Flows | No Flow |
| IX | — | Flows | Flows | No Flow |
| X | — | Flows | Flows | No Flow |
| XI | — | Flows | Flows | Flows[2] |
| XII | — | Flows | Flows | Flows |

[1]Without additives, flows at −20° F.
[2]Marginal Flow.

TABLE III

Commercial 5W30 Oil "Brand B"[1]
After 16 Hours at −22° F.

| Additive | 1% | 2% | 3% | 4% |
|---|---|---|---|---|
| A | Flows | No Flow | — | — |
| B | Flows | Flows | No Flow | — |
| C | Flows | Flows | No Flow | — |
| III | — | Flows | Flows | Flows |
| IV | — | Flows | Flows | Flows |
| VI | — | Flows | Flows | No Flow |
| VII | — | Flows | Flows | Flows[2] |
| VIII | — | Flows | Flows | Flows[2] |
| IX | — | Flows | Flows | No Flow |

[1]Without additives, flows at −22° F.
[2]Marginal Flow.

TABLE IV

Commercial 10W40 Oil "Brand C"[1]
After 16 Hours at −20° F.

| Additive | 1% | 2% | 3% | 4% |
|---|---|---|---|---|
| A | Flows | No Flow | — | — |
| B | — | Flows | Flows | Flows |
| III | — | — | Flows | Flows |
| VI | — | Flows | Flows | Flows |
| VII | — | — | Flows | Flows |

[1]Without additives, flows at −20° F.

TABLE V

Falex Step-Up Test, 10W40 Oil, "Brand A"

| | Lbs. Load Before Failure | Torque at 1500 lbs. |
|---|---|---|
| Oil alone | 1250 | (45 at 1250) |
| 2% B | 1500 | 30 |
| 2% C | 1500 | 30 |
| 2% III | 1750 | 25 |
| 3% IV | 2000 | 24 |
| 2% VII | 1750 | 26 |
| 3% VII | 1750–2000 | 25 |
| 3% VIII | 2000 | 23 |
| 2% IX | 1750–2000 | 27 |
| 3% IX | 2000 | 27 |
| 3% X | 1750 | 28 |
| 2% XI | 1750 | 25 |
| 3% XI | 2250 | 24 |
| 2% XII | 1500–1750 | 27 |
| 3% XII | 1750 | 26 |
| 4% XII | 2000 | 25 |

TABLE VI

Falex Step-Up Test in Non-Formulated Base Hydrocarbons

| | Lbs. Load Before Failure | Torque at 1250 |
|---|---|---|
| Mid-Continent Oil | 750 | — |
| Oil + 2% VI | 1250–1500 | 24 |
| Gulf Synfluid 4cs | 250–500 | — |
| Gulf Synfluid 4cs | | |
| + 2% VIII | 1250–1500 | 19 |

What is claimed is:

1. A sulfurized, triglyceride additive composition, comprising a sulfurized, transesterified triglyceride wherein the total acid component of the triglyceride comprises no less than about 35 mole % saturated aliphatic acids and no more than about 65 mole % unsaturated fatty acids, said total acid component being further characterized as comprising:
   (a) more than about 20 mole % of mono-unsaturated acids;
   (b) less than about 15 mole % of poly-unsaturated fatty acids;
   (c) more than about 20 mole % saturated aliphatic acids having 6 to 16 carbon atoms, including more than about 10 mole % saturated aliphatic acids having 6 to 14 carbon atoms; and
   (d) less than about 15 mole % saturated aliphatic acids having 18 or more carbon atoms.

2. The sulfurized triglyceride additive composition of claim 1, wherein said mono-unsaturated fatty acids are present in an amount greater than about 35 mole %.

3. The sulfurized triglyceride additive composition of claim 1, wherein said poly-unsaturated fatty acids are present in an amount less than about 10 mole %.

4. The sulfurized triglyceride additive composition of claim 1, wherein said total saturated aliphatic acids are present in an amount greater than about 50 mole %.

5. The sulfurized triglyceride additive composition of claim 1, wherein said saturated acids having 6 to 14 carbon atoms are present in an amount greater than about 15 mole %.

6. The sulfurized triglyceride additive composition of claim 1, wherein said saturated acids having 6 to 16 carbon atoms are present in an amount greater than about 35 mole %.

7. The sulfurized triglyceride additive composition of claim 1, additionally comprising a solubilization agent.

8. The sulfurized triglyceride additive composition of claim 7 wherein the solubilization agent is selected from the group consisting of triglycerides, olefins, esters of unsaturated carboxylic acids, and mixtures thereof.

9. The sulfurized triglyceride additive composition of claim 8 wherein the solubilization agent is a triglyceride.

10. The sulfurized triglyceride additive composition of claim 8 wherein the solubilization agent is an olefin.

11. The sulfurized triglyceride additive composition of claim 10 wherein the olefin contains from about 8 to about 20 carbon atoms, alone or in mixtures thereof.

12. The sulfurized triglyceride additive composition of claim 8 wherein the solubilization agent is an ester of an unsaturated carboxylic acid.

13. The sulfurized triglyceride additive composition of claim 7 wherein the solubilization agent is present in an amount within the range from about 5 wt. % to about 70 wt. % based on the transesterified triglyceride.

14. The sulfurized triglyceride additive composition of claim 13 wherein the solubilization agent is present in an amount within the range from about 5 wt. % to about 55 wt. %, based on the transesterified triglyceride.

15. The sulfurized triglyceride additive composition of claim 1 wherein bound sulfur is present in an amount within the range from about 4 wt. % to about 14 wt. %, based on the total product.

16. A method for preparing a sulfurized, transesterified triglyceride additive composition, comprising the steps of:
(1) transesterifying one or more triglycerides with one or more organic acids, or esters thereof, to yield a transesterified triglyceride wherein the total acid component comprises no less than about 35 mole % saturated aliphatic acids and no more than about 65 mole % unsaturated fatty acids, said total acid component being further characterized as comprising:
  (a) more than about 20 mole % of monounsaturated fatty acids;
  (b) less than about 15 mole % of polyunsaturated fatty acids;
  (c) more than about 20 mole % saturated aliphatic acids having 6 to 16 carbon atoms, including more than about 10 mole % saturated aliphatic acids having 6 to 14 carbon atoms; and
  (d) less than about 15 mole % saturated aliphatic acids having 18 or more carbon atoms; and
(2) sulfurizing the transesterified triglyceride product mixture of step 1 with elemental sulfur to incorporate bound sulfur in an amount within the range from about 4 wt. % to about 14 wt. %, based upon the transesterified triglyceride product mixture.

17. The method of claim 16, wherein said monounsaturated fatty acids are present in an amount greater than about 35 mole %.

18. The method of claim 16, wherein said polyunsaturated fatty acids are present in an amount less than about 10 mole %.

19. The method of claim 16, wherein said total saturated aliphatic acids are present in an amount greater than about 50 mole %.

20. The method of claim 16, additionally comprising the step of esterifying free acids in the tranesterification reaction product with an alcohol component prior to the sulfurization step.

21. The method of claim 20 wherein said alcohol component for esterification comprises branched chain aliphatic primary alcohols.

22. The method of claim 16, additionally comprising the step of blending said transesterification reaction product with a compound selected from the group consisting of triglycerides, esterified fatty acids, α-olefins and mixtures thereof, prior to the sulfurization step.

23. The method of claim 16 wherein said transesterification step is carried out in the presence of a transesterification catalyst.

24. The method of claim 23 wherein said transesterification catalyst is selected from the group consisting of tetrabutyl titanate, zinc acetate, sodium carbonate, sodium sulfate, stannous oxalate, p-toluenesulfonic acid, methanesulfonic acid, sulfuric acid, butylchlorotin dihydroxide, and phosphoric acid.

25. The method of claim 23 wherein said transesterification catalyst is present in an amount within the range from about 0.01 to about 1 wt. %, based on the triglycerides.

26. The method of claim 25 in which said catalyst is present in an amount within the range from about 0.03 to about 0.5 wt. %.

27. The method of claim 24 wherein said catalyst is p-toluenesulfonic acid.

28. The method of claim 24 wherein said catalyst is methanesulfonic acid.

29. A lubricating oil composition, comprising:
(1) a refined base oil, having lubricating oil viscosity and volatility properties; and
(2) a minor amount, from about 0.05 to about 15 wt. % of the lubricating oil composition, of a sulfurized triglyceride additive composition, comprising a sulfurized, transesterified triglyceride wherein the total acid component of the triglyceride comprises no less than about 35 mole % saturated aliphatic acids and no more than about 65 mole % unsaturated fatty acids, said total acid component being further characterized as comprising:
  (a) more than about 20 mole % of mono-unsaturated acids;
  (b) less than about 15 mole % of poly-unsaturated fatty acids;
  (c) more than about 20 mole % saturated aliphatic acids having 6 to 16 carbon atoms, including more than about 10 mole % saturated aliphatic acids having 6 to 14 carbon atoms; and
  (d) less than about 15 mole % saturated aliphatic acids having 18 or more carbon atoms.

30. The lubricating oil composition of claim 29 wherein the sulfurized triglyceride additive composition is present in an amount within the range from about 0.5 to about 5 wt. % of the lubricating oil composition.

31. A fuel composition, comprising:
(1) a blended base fuel, having suitable volatility and combustion properties; and
(2) a minor amount, from about 0.0005 to about 0.1 wt. % of the fuel composition, of a sulfurized triglyceride additive composition, comprising a sulfurized, transesterified triglyceride wherein the total acid component of the triglyceride comprises no less than about 35 mole % saturated aliphatic acids and no more than about 65 mole % unsaturated fatty acids, said total acid component being further characterized as comprising:
  (a) more than about 20 mole % of mono-unsaturated acids;
  (b) less than about 15 mole % of poly-unsaturated fatty acids;
  (c) more than about 20 mole % saturated aliphatic acids having 6 to 16 carbon atoms, including more than about 10 mole % saturated aliphatic acids having 6 to 14 carbon atoms; and
  (d) less than about 15 mole % saturated aliphatic acids having 18 or more carbon atoms.

32. The fuel composition of claim 31 wherein the blended base fuel is a gasoline fuel, for use in a spark-ignition internal combustion engine.

33. The fuel composition of claim 31 wherein the blended base fuel is a diesel fuel, for use in a compression-ignition internal combustion engine.

34. The fuel composition of claim 31 wherein the blended base fuel is a heating oil, for use in an oil-fired burner assembly.

35. The fuel composition of claim 31 wherein the sulfurized triglyceride additive composition is present in an amount within the range from about 0.0015 to about 0.05 wt. % of the fuel composition.

* * * * *